United States Patent [19]

Dennick

[11] Patent Number: 5,260,305
[45] Date of Patent: Nov. 9, 1993

[54] COMBINATION OF PRAVASTATIN AND NICOTINIC ACID OR RELATED ACID AND METHOD FOR LOWERING SERUM CHOLESTEROL USING SUCH COMBINATION

[75] Inventor: Leonard G. Dennick, Princeton, N.J.

[73] Assignee: E. R. Squibb & Sons, Inc., Princeton, N.J.

[21] Appl. No.: 900,378

[22] Filed: Jun. 18, 1992

Related U.S. Application Data

[63] Continuation-in-part of Ser. No. 817,233, Jan. 6, 1992, abandoned, which is a continuation of Ser. No. 535,260, Jun. 8, 1990, abandoned, which is a continuation-in-part of Ser. No. 282,647, Dec. 12, 1988, abandoned.

[51] Int. Cl.⁵ ............... A61K 31/495; A61K 31/44; A61K 31/34; A61K 31/225
[52] U.S. Cl. .................... 514/255; 514/356; 514/473; 514/547; 514/824
[58] Field of Search ............... 514/451, 356, 255, 473, 514/547, 824

[56] References Cited

U.S. PATENT DOCUMENTS

| | | | |
|---|---|---|---|
| 3,674,836 | 7/1972 | Creger | 260/408 |
| 4,027,009 | 5/1977 | Grier et al. | 424/78 |
| 4,231,938 | 11/1980 | Monaghan et al. | 560/256 |
| 4,346,227 | 8/1982 | Terahara et al. | 514/451 |
| 4,448,784 | 5/1984 | Glamkowski et al. | 548/491 |
| 4,450,171 | 5/1984 | Hoffman et al. | 549/292 |
| 4,759,923 | 7/1988 | Buntin et al. | 514/183 |

OTHER PUBLICATIONS

Abstract "Comparative Efficacy and Safety of Pravastatin, Nicotinic Acid, and the Two Combined in Patients with Hypercholesterolemia," 9th International Symposium on Atherosclerosis, Rosemont, Ill., Oct. 6-11, 1991.
New England Journal of Med., Nov. 3, 1988, p. 1222.
New England Journal of Med., vol. 319:24-33, Jul. 7, 1988.
Physicians' Desk Ref. (PDR) 42nd Ed. (1988), pp. 638, 757, 1417 and 1589.
J. Clin. Med., Feb. 1977, pp. 354-366.
Kane, et al. "Normalization of Low-Density-Lipoprotein Levels in Heterozygous Familial Hypercholesterolemia with a Combined Drug Regimen".
JAMA, Jun. 19, 1987, vol. 257, No. 23, pp. 3233-3240.
Merck Index, Eleventh Edition-p. 108 and App-1 (1988).
Drug Future, 1987, 12, 349.

Primary Examiner—Frederick E. Waddell
Assistant Examiner—Raymond J. Henley, III
Attorney, Agent, or Firm—Burton Rodney

[57] ABSTRACT

A pharmaceutical combination is provided which includes an inhibitor of the enzyme 3-hydroxy-3-methylglutaryl coenzyme A (HMG CoA) reductase, which is pravastatin and a pharmaceutical which reduces serum cholesterol and/or inhibits cholesterol biosynthesis by a mechanism other than inhibiting production of the enzyme HMG CoA reductase, namely, nicotinic acid (niacin) or related acid. A method for reducing serum cholesterol or inhibiting formation of or treating atherosclerosis using the above combination without causing drug-induced myopathy or rhabdomyolysis, is also provided.

9 Claims, No Drawings

COMBINATION OF PRAVASTATIN AND NICOTINIC ACID OR RELATED ACID AND METHOD FOR LOWERING SERUM CHOLESTEROL USING SUCH COMBINATION

REFERENCE TO OTHER APPLICATIONS

This application is a continuation-in-part of application Ser. No. 07/817,233, filed Jan. 6, 1992, now abandoned, which is a continuation of application Ser. No. 07/535,260, filed Jun. 8, 1990, now abandoned, which is a continuation-in-part of application Ser. No. 07/282,647, filed Dec. 12, 1988, now abandoned.

FIELD OF THE INVENTION

The present invention relates to a combination of an inhibitor of 3-hydroxy-3-methylglutaryl coenzyme A (HMG CoA) reductase which is pravastatin and nicotinic acid or related acid which reduces serum cholesterol other than by inhibiting the enzyme HMG CoA reductase, and to methods for lowering serum cholesterol and triglycerides and/or preventing or treating atherosclerosis and/or elevated triglycerides by administering such combination. The above methods may be carried out without causing drug- induced myopathy or rhabdomyolysis.

BACKGROUND OF THE INVENTION

There are several different classes of compounds which have serum cholesterol lowering properties. Some of these compounds are inhibitors of the enzyme HMG CoA reductase which is essential in the production of cholesterol, such as mevastatin (disclosed in U.S. Pat. No. 3,983,140), lovastatin also referred to as mevinolin (disclosed in U.S. Pat. No. 4,231,938), pravastatin (disclosed in U.S. Pat No. 4,346,227) and velostatin also referred to as synvinolin (disclosed in U.S. Pat. Nos. 4,448,784 and 4,450,171).

Other compounds which lower serum cholesterol may do so by an entirely different mechanism than the HMG CoA reductase inhibitors. For example, serum cholesterol may be lowered through the use of bile acid sequestrants such as cholestyramine, colestipol, DEAE-Sephadex and poly(diallylmethylamine) derivatives (such as disclosed in U.S. Pat. Nos. 4,759,923 and 4,027,009) or through the use of antihyperlipoproteinemics such as probucol and gemfibrozil which apparently lower serum lower density lipoproteins (LDL) and/or converts LDL into high density lipoproteins (HDL).

U.S. Pat. No. 4,759,923 mentioned above discloses that poly(diallylmethylamine) derivatives which are bile salt sequestrants may be used in conjunction with drugs which reduce serum cholesterol by mechanisms other than sequestration, such as clofibrate, nicotinic acid, probucol, neomycin, p-aminosalicylic acid or mevinolin (also referred to as lovastatin).

Other known cholesterol lowering agents include derivatives of nicotinic acid, namely 5-methylpyrazine-carboxylic acid 4-oxide (acipimox), 4,5-dihydro-5-methyl-4-oxo-5-phenyl- 2-furancarboxylic acid (acifran) and nicotinic acid N-oxide-2-t-butyl-4-cyclohexylphenyl ester, the latter being disclosed in Drug. Fut., 1987, 12, 349.

Grundy, S. M. "HMG-CoA Reductase Inhibitors for Treatment of Hypercholesterolemia," N. Eng. J. Med. Vol. 319 No. 1 pp 24–33, discloses that pravastatin by itself and nicotinic acid by itself are known cholesterol lowering drugs.

At page 28, column 2, Grundy discloses that combinations of lovastatin and gemfibrozil may be associated with an increased frequency of drug induced myopathy.

At page 29, lines 7 to 11, Grundy discloses that "recent clinical experience suggests that the combination of lovastatin and cyclosporine, gemfibrozil, or niacin may predispose patients to myopathy and occasionally even to rhabdomyolysis."

At page 30, column 1, starting at the last six lines from the bottom Grundy indicates that "the combination of lovastatin and niacin has not been shown to be safe in a controlled clinical trial."

Physicians' Desk Reference, 44th Ed., 1990, page 1413, reports that severe cases of rhabdomyolysis have been associated in patients receiving lovastatin in combination with either gemfibrozil or lipid-lowering doses of nicotinic acid.

It is now believed that hypertriglyceridemia may be an independent risk factor for coronary artery disease, particularly in vulnerable populations, such as in diabetics. Furthermore, many individuals with hypercholesterolemia also have elevated triglyceride levels (mixed hyperlipidemia). In such cases, a reduction in triglyceride concentrations can also result in the secondary lowering of cholesterol.

It is also known that patients with severe hypertriglyceridemia are at risk for developing pancreatitis.

DESCRIPTION OF THE INVENTION

In accordance with the present invention, a pharmaceutical combination is provided for use in reducing serum cholesterol and triglycerides and in inhibiting formation of or treating atherosclerosis, without causing drug induced myopathy, which combination is formed of the 3-hydroxy-3-methylglutaryl coenzyme A (HMG CoA) reductase inhibitor pravastatin and a pharmaceutical (also referred to as other serum cholesterol lowering agent) which reduces serum cholesterol and triglycerides and/or inhibits cholesterol biosynthesis by a mechanism other than by inhibiting production of the enzyme HMG CoA reductase, such as an antihyperlipoproteinemic agent which is nicotinic acid (niacin) or related acid derivatives thereof such as acipimox, acifran and nicotinic acid N-oxide-2-t-butyl-4-cyclohexylphenyl ester, which inhibits formation of LDL or converts LDL to HDL and/or reduces triglycerides.

The HMG CoA reductase inhibitor pravastatin will be employed in a weight ratio to the "pharmaceutical" of within the range of from about 0.001:1 to about 1000:1 and preferably from about 0.05:1 to about 100:1.

In addition, in accordance with the present invention, a method is provided for lowering serum cholesterol and/or reducing triglycerides or inhibiting formation of or treating atherosclerosis and/or elevated triglycerides wherein a therapeutically effective amount of the above combination is systemically, such as orally or parenterally, administered over a prolonged period.

It has also been found that the combination of the HMG CoA reductase inhibitor pravastatin and other serum cholesterol lowering agent, which works by a mechanism other than inhibiting HMG CoA reductase, is a surprising and unique concept in inhibiting or treating elevated cholesterol and/or triglycerides and/or atherosclerosis in that it may provide additional anti-cholesterolemic effects and/or anti-triglycerides effects over that which may be obtained using each of the components of the combination alone. In fact, it has been found that the pharmaceutical combination of the invention lowers triglycerides to a substantially greater extent than each of the components of the combination alone.

In addition, the combination of the invention which includes compounds with different mechanisms of action, may be used to effectively treat cholesterol-related diseases of multiple etiology.

Surprisingly, the pharmaceutical combination of the invention produces the above benefits without causing myopathy or rhabdomyolysis.

The "pharmaceutical" or other serum cholesterol lowering agents which function other than by inhibiting the enzyme HMG CoA reductase suitable for use herein include, antihyperlipoproteinemic agents such as nicotinic acid (niacin), acipimox, nicotinic acid N-oxide-2-t-butyl-4- cyclohexylphenyl ester, or acifran or other known derivatives of nicotinic acid which are antihyperlipoproteinemic agents.

Preferred are combinations of pravastatin with niacin or acipimox.

The disclosure of the above-mentioned U.S. patents and U.S. patent applications are incorporated herein by reference.

In carrying out the method of the present invention, the combination of the invention may be administered to mammalian species, such as dogs, cats, humans, etc. and as such may be incorporated in a conventional systemic dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like. Oral dosage forms are preferred, although parenteral forms are quite satisfactory as well.

The dose administered must be carefully adjusted according to age, weight and condition of the patient, as well as the route of administration, dosage form and regimen and the desired result.

Thus, for oral administration, a satisfactory result may be obtained employing pravastatin in dosages as indicated in the Physician's Desk Reference, such as in an amount within the range of from about 1 to 2000 mg and preferably from about 4 to about 200 mg, more preferably from about 5 to about 80 mg, in combination with the nicotinic acid or related acid in dosages normally employed as indicated in the Physician's Desk Reference, for nicotinic acid such as in an amount within the range of from about 50 mg to about 1000 mg and preferably from about 75mg to about 800 mg, with the HMG CoA reductase inhibitor and nicotinic acid or related acid being employed together in the same oral dosage form or in separate oral dosage forms taken at the same time.

A preferred oral dosage form, such as tablets or capsules, will contain the HMG CoA reductase inhibitor in an amount of from about 0.5 to about 100 mg, preferably from about 5 to about 80 mg, and more preferably from about 10 to about 40 mg, and the nicotinic acid or related acid in an amount of from about 2 to about 3000 mg, preferably from about 2 to about 2000 mg.

The composition described above may be administered in the dosage forms as described above in single or divided doses of one to four times daily. It may be advisable to start a patient on a low dose combination and work up gradually to a high dose combination.

Tablets of various sizes can be prepared, e.g., of about 2 to 2000 mg in total weight, containing one or both of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonsful.

Such dosage forms can be administered to the patient on a regimen of one to four doses per day According to another modification, in order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

Fixed combinations of pravastatin and the other serum cholesterol lowering agent are more convenient and are preferred, especially in tablet or capsule form for oral administration.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

Some of the active substances described: above form commonly known, pharmaceutically acceptable salts such as alkali metal and other common basic salts or acid addition salts, etc. References to the base substances are therefore intended to include those common salts known to be substantially equivalent to the parent compound.

The formulations as described above will be administered for a prolonged period, that is, for as long as the potential for elevated serum cholesterol and atherosclerosis remains or the symptoms continue. Sustained release forms of such formulations which may provide such amounts biweekly, weekly, monthly and the like may also be employed. A dosing period of at least one to two weeks are required to achieve minimal benefit.

The following Examples represent preferred embodiments of the present invention. All temperatures are expressed in degrees Centigrade unless otherwise indicated and all mesh sizes are U.S. Standard ASTME.

EXAMPLE 1

A pravastatin formulation in the form of tablets having the following composition was prepared as described below.

| Ingredient | Parts by Weight |
|---|---|
| Pravastatin | 7 |
| Lactose | 67 |
| Microcrystalline cellulose | 20 |
| Croscarmellose sodium | 2 |
| Magnesium stearate | 1 |
| Magnesium oxide | 3 |

Pravastatin, magnesium oxide and a fraction (30%) of the lactose were mixed together for 2 to 10 minutes employing a suitable mixer. The resulting mixture was passed through a #12 to #40 mesh size screen. Microcrystalline cellulose, croscarmellose sodium and the remaining lactose were added and the mixture was mixed for 2 to 10 minutes. Thereafter, magnesium stearate was added and mixing was continued for 1 to 3 minutes.

The resulting homogeneous mixture was then compressed into tablets each containing 5 mg, 10 mg, 20 or 40 mg pravastatin.

Niacin tablets containing 250 mg niacin are prepared employing conventional procedures containing ingredients as set out in the 1990 PDR.

The pravastatin tablets and niacin tablets may be administered as a combination in accordance with the teachings of the present invention to lower serum cholesterol and/or treat atherosclerosis. In addition, the pravastatin and niacin tablets may be ground up into powders and used together in a single capsule.

EXAMPLES 2 AND 3

Pravastatin tablets are prepared employing conventional pharmaceutical techniques containing 20 mg pravastatin, cellulose, color, lactose, magnesium stearate and starch and butylated hydroxyanisole as a preservative as described in the 1991 PDR.

The pravastatin tablets may be employed in combination with the niacin tablets (described in Example 1) in separate or combined dosage forms to treat elevated serum cholesterol or atherosclerosis in accordance with the present invention.

EXAMPLES 4 AND 5

Pravastatin tablets described in Examples 1 and 2, respectively, may be employed in combination with acipimox capsules containing 750 mg acipimox and inactive ingredients as described in the 1991 PDR with respect to niacin. The pravastatin and acipimox may be employed in separate dosage forms or combined in a single capsule form to lower elevated serum cholesterol or treat atherosclerosis in accordance with the present invention.

EXAMPLES 6 AND 7

Pravastatin tablets described in Examples 1 and 2, respectively, may be employed in combination with acifran capsules containing 750 mg acifran and inactive ingredients as described in the 1991 PDR with respect to niacin. The pravastatin and acifran may be employed in separate dosage forms or combined in a single capsule form to lower elevated serum cholesterol or treat atherosclerosis in accordance with the present invention.

EXAMPLE 8

The following study in humans was carried out to determine comparative efficacy and safety of pravastatin, nicotinic acid, and the two combined in patients with hypercholesterolemia.

It is known that nicotinic acid (NA) is used as an antihyperlipidemic drug in almost all types of primary hyperlipidemia. It is also known that pravastatin sodium (P) is used in type IIa and IIb primary hypercholesterolemia. The following describes a study which compared the efficacy and safety of NA, P and their combination a double-blind, placebo (PLA)-controlled study.

After 6 weeks of diet (AHAI) and placebo (PLA) lead-in, 157 type IIa or IIb primary hypercholeserolemic, patients (FH or non-FH) were randomized to 8 weeks of treatment of either PLA, P 40 mg at bedtime, NA 1 g BID (as extended-release capsules) or P+NA. The patients were blinded to P and PLA only. For randomization, the mean of 2 baseline low-density lipoprotein cholesterol (LDL-C) levels had to be >75th percentile for the US population, adjusted for age and sex, and $\geq$150 mg/dl. Triglycerides (TG) had to be $\leq$350 mg/dl. Intent-to-treat statistical analysis was performed on lipids by covariance, using $\alpha=0.05$ and $\beta=0.2$. The mean percentage changes from baseline in lipids and safety assessments at week 8 are summarized as below.

|  | LDL-C | TC | HDL-C | TG | ALAT | ASAT | CK |
|---|---|---|---|---|---|---|---|
| PLA | −4.2 | −3.1 | −0.4 | −7.7 | −1.0 | −2.3 | −2.4 |
| NA | −16.2[123] | +11.4[123] | +12.9 | −12.4[14] | +59.8[12] | +33.2[125] | +18.3[1] |
| P | −33.3[124] | −23.5[124] | +13.9[12] | −14.0[14] | +24.6[1] | +7.7[4] | −4.7 |
| NA + P | −42.8[12] | −32.9[12] | +15.4[12] | −34.8[12] | +54.6[12] | +39.8[12] | +9.8 |

[1]Significantly different vs baseline
[2]Significantly different vs placebo
[3]Significantly different vs P and P + NA
[4]Significantly different vs P + NA only
[5]Significantly different vs P only
($P \leq 0.05$ range = 0.001 to 0.05)

The study shows that myopathy and rhabdomyolysis were not induced in patients treated with pravastatin, nicotinic acid and a combination of pravastatin and nicotinic acid.

In addition, as seen, the effect of the combination of pravastatin and nicotinic acid on triglycerides (−34.3% change from baseline) is substantially more than the effect of pravastatin alone on triglycerides (−12.6% change from baseline), and the effect of nicotinic acid alone on triglycerides (−9.7% change from baseline) and the effect of placebo on triglycerides (−3.4% change from baseline).

What is claimed is:

1. A pharmaceutical combination comprising a therapeutically effective amount of pravastatin and a therapeutically effective amount of nicotinic acid or a derivative of nicotinic acid which has antihypercholesterolemic activity and will not cause drug-induced myopathy or rhabdomyolysis, wherein the pravastatin is employed in an amount within the range of from about 10 to about 40 mg and the nicotinic acid or derivative thereof is employed in an amount within the range of from about 75 to about 2000 mg.

2. The combination as defined in claim 1 wherein the derivative of nicotinic acid is acipimox, acifran or nicotinic acid N-oxide 2-t-butyl-4-cyclohexylphenyl ester.

3. The combination as defined in claim 1 wherein pravastatin is in combination with nicotinic acid or acipimox.

4. A method for lowering serum cholesterol or inhibiting formation of or treating atherosclerosis, without causing drug-induced myopathy or rhabdomyolysis, which comprises administering to a patient in need of such treatment a therapeutically effective amount of a pharmaceutical combination comprising a therapeutically effective amount of pravastatin and a therapeutically effective amount of nicotinic acid or a derivative of nicotinic acid, wherein pravastatin is employed in an amount within the range of from about 10 to about 40 mg per day and the nicotinic acid derivative thereof is employed in an amount within the range of from about 75 to about 2000 mg per day.

5. The method as defined in claim 4 wherein the derivative of nicotinic acid is acipimox, acifran or nicotinic acid N-oxide-2-t-butyl-4-cyclohexylphenyl ester.

6. The method as defined in claim 4 wherein cholesterol is lowered without causing myopathy or rhabdomyolysis.

7. A hypocholesterolemic or hypolipemic composition comprising pravastatin and nicotinic acid or a derivative of nicotinic acid, and a pharmaceutically acceptable carrier therefor wherein the pravastatin is employed in an amount within the range of from about 10 to about 40 mg and the nicotinic acid derivative thereof is employed in an amount within the range of from about 75 to about 2000 mg.

8. A method for lowering triglycerides without causing drug-induced myopathy or rhabdomyolysis, which comprises administering to a patient in need of such treatment a therapeutically effective amount of a pharmaceutical combination comprising a therapeutically effective amount of pravastatin and a therapeutically effective amount of nicotinic acid or derivative of nicotinic acid, wherein the pravastatin is employed in an amount within the range of from about 10 to about 40 mg per day and the nicotinic acid or derivative thereof is employed in an amount within the range of from about 1000 to about 2000 mg per day.

9. The method as defined in claim 8 wherein the derivative of nicotinic acid is acipimox, acifran or nicotinic acid N-oxide-2-t-butyl-4-cyclohexylphenyl ester.

* * * * *